United States Patent [19]
Love

[11] Patent Number: 4,470,157
[45] Date of Patent: Sep. 11, 1984

[54] TRICUSPID PROSTHETIC TISSUE HEART VALVE

[76] Inventor: Jack W. Love, 785 Carosam Rd., Santa Barbara, Calif. 93110

[21] Appl. No.: 486,376

[22] Filed: Apr. 19, 1983

Related U.S. Application Data

[63] Continuation-in-part of Ser. No. 257,990, Apr. 27, 1981, abandoned.

[51] Int. Cl.³ ............................................. A61F 1/22
[52] U.S. Cl. ...................................................... 3/1.5
[58] Field of Search ...................................... 3/1.5, 1

[56] References Cited

U.S. PATENT DOCUMENTS

| | | | |
|---|---|---|---|
| 3,714,671 | 2/1973 | Edwards et al. | 3/1.5 |
| 3,755,823 | 9/1973 | Hancock | 3/1.5 |
| 4,035,849 | 7/1977 | Angell et al. | 3/1.5 |
| 4,084,268 | 4/1978 | Ionescu et al. | 3/1.5 |
| 4,172,295 | 10/1979 | Batten | 3/1.5 |
| 4,192,020 | 3/1980 | Davis et al. | 3/1.5 |

OTHER PUBLICATIONS

"Frame-Mounted Tissue Heart Valves: Technique of Construction" by I. T. Bartek et al., Thorax (1974) 29, 51, pp. 51–55.

*Primary Examiner*—Ronald L. Frinks
*Attorney, Agent, or Firm*—Freilich, Hornbaker, Rosen & Fernandez

[57] ABSTRACT

A method and apparatus for providing a tricuspid heart valve that can be assembled with autogenous or foreign tissue using a prefabricated kit comprised of two stents that mate together and a sewing ring, one stent inside or below the other, with the tissue clamped between the stents. The inner or lower stent has a scalloped wall to provide three equally spaced peaks extending from an annular base. The stents may have interlocking means at or near their base to not only lock them together, but also to clamp the tissue in place more securely. In the case of having the one stent inside the other, both stents may have a scalloped wall. The tissue is first placed over the inner stent, then after the outer stent is placed over the tissue, excess tissue is trimmed. The mated stents secure the tissue securely in place. The outer stent may have a ledge along its upper edge overhanging the inner stent to clamp the tissue. In the case of having one stent below the other, the upper stent may be a short cylinder scalloped at both ends to fit as a cap over the lower stent. Alternatively, the upper stent may be formed from three sections of bent rods welded at the peaks. In either case, the upper stent fits closely as a cap over the lower stent, and the lower stent may have an annular base or a scalloped base. In each embodiment, the stents may be made of thermoplastic material and covered by fabric that is thermobonded, i.e., secured to the stents by applying heat and pressure to at least selected areas.

31 Claims, 18 Drawing Figures

TRICUSPID PROSTHETIC TISSUE HEART VALVE

CROSS-REFERENCE TO RELATED APPLICATION

This application is a continuation-in-part of application Ser. No. 06/257,990, filed Apr. 27, 1981, now abandoned.

BACKGROUND OF THE INVENTION

This invention relates to a method and apparatus for providing a prosthetic heart valve of the tricuspid tissue type assembled from the patient's autogenous tissue from a prefabricated kit comprising two stents, one to crimp the tissue against the other, in order to establish the geometry of the tissue valve, and a sewing ring.

Early successes in the use of prosthetic tissue heart valves have led to their more widespread use. The valves have generally been fabricated from animal tissue in various sizes and stored in a stabilizing and preserving solution until needed. It would be desirable to employ a device for fabricating a prosthetic heart valve from the patient's autogenous (pericardial or other) tissue taken from the patient at the time of the implant. The tissue would then be accepted as a graft by the host, and endure indefinitely. But tissue valves which have heretofore been known require as much as 3 to 6 hours to assemble. The patient cannot be safely maintained in surgery the extra hours that would be required to assemble a prosthetic valve of the prior-art type. Consequently, prior-art tissue valves have been preassembled with animal tissue and preserved until needed. What is required is a device which takes only a few minutes to assemble into a prosthetic valve once autogenous tissue is taken from the patient. Such a device would, of course, also be useful in constructing a prosthetic heart valve in advance of surgery with tissue from some other source, such as bovine pericardium.

SUMMARY OF THE INVENTION

In accordance with the broadest aspects of the present invention, a method and apparatus is provided for assembling a tricuspid tissue heart valve from autogenous or other tissue using two prefabricated stents that mate together, one inside or below the other, with tissue secured therebetween. In one embodiment most useful for atrio-ventricular valves, one stent fits inside the other. Each stent has an annular base, and at least the inner stent is scalloped to provide three equally spaced peaks extending from the annular base. Both stents are covered with bonded fabric. Tissue is first placed over the inner stent. Then the outer stent is placed over the tissue covered inner stent. Securing the inner and outer stents together, with the tissue secured therebetween, completes the assembly, except for an annular sewing ring which is secured to the base of the two-stent assembly.

The outer stent may be made with a ledge overhanging the upper edge of the inner stent. When the outer stent is placed over the inner stent, the ledge of the outer stent clamps the tissue against the scalloped upper edge of the inner stent to secure it more firmly in place and to keep the tissue valve in the closed position. Alternatively, or additionally, the inner and outer stents may have interlocking means which further clamp the tissue in place. The outer stent may be split on one side so it can be opened widely while it is placed over the tissue on the inner stent, particularly when interlocking grooves are provided in the two stents. In another embodiment, a second stent is provided which does not have an annular base, and is instead a scalloped cap that fits on the scalloped wall of the first stent. The second stent may be formed of three sections of bent rods welded at the peaks. For prosthetic aortic valves, the first stent may also have the same scalloped shape as the second (cap) stent just described. Instead of fitting the second stent on top of the first as a cap, it may be made with an inner diameter only slightly larger than the outer diameter of the first stent to fit closely around the first stent.

The novel features that are considered characteristic of this invention are set forth with particularity in the appended claims. The invention will best be understood from the following description when read in connection with the accompanying drawings.

DESCRIPTION OF PREFERRED EMBODIMENTS

The basic concept of the invention will first be described with reference to FIGS. 1 and 2 for fabricating a prosthetic tissue heart valve 10 shown in FIG. 3 from a patient's autogenous tissue, such as pericardium taken from the patient at the time of surgery, or foreign tissue, such as bovine pericardium. The valve is fabricated from elements shown in FIG. 1 comprising two stents 11 and 12 that mate together with tissue 13 secured between the stents. The tissue may be preformed into a cylinder, as shown, or placed in one or more sections on the inner stent 11. The stents are prefabricated in a variety of sizes to permit selection of a size which best fits a patient and are covered with cloth, such as Dacron bonded to the stents which are preferably made of Delrin, a thermoplastic acetal resin. Since Delin has a lower melting temperature than Dacron, it is possible to apply heat and pressure to the fabric over the stents for a period sufficient for the surface of the stents to melt and flow into the interstices of the fabric. This thermobonding may be applied uniformly, but in practice it may be sufficient to apply it only at selected spots.

Each stent is a cylinder having a scalloped end opposite an annular base. Referring to the inner stent 11, it has a base 14 and three pointed peaks 15 spaced 120° apart with a smooth scalloped wall between the posts at the end opposite the base. The stent 12 is similarly a scalloped cylinder having three equally spaced peaks 16, but with rounded tips at the end opposite a base 17. A flexible flange 18 attached to the base 17 of the stent 12 is used to sew the assembled valve in the patient's heart in a well known manner.

To assemble the valve, the tissue cylinder 13 is formed from a rectangular section of tissue. In most cases, the rectangular section of tissue required to form the cylinder will be in a single piece, as shown in FIG. 1, but in some cases three smaller pieces may be cut and formed into a cylinder by stapling or stitching the sections together. In order that the inner diameter of the tissue cylinder closely match the outside diameter of the stent 11, a mandril is used to form the tissue cylinder which is then slipped off one end of the mold as staples or stitches 19 are put in place. The tissue cylinder is next slipped over the inner stent 11, as shown in FIG. 2. Alternatively, tissue in one or more sections is placed directly over the inner stent to form webs between the peaks. The outer stent 12 is then placed over the tissue with its rounded peaks 16 centered over the pointed peaks 15 of the inner stent. The tissue is fastened together around each post, as by a stitch or clip 20, as shown in FIG. 3, thereby to cause the edges of the tissue web between the posts to collapse inwardly against each other in a "closed" position. Any pressure differential will force blood to flow through the inside of the inner stent past the tissue, causing its edges to separate. Once the pressure differential terminates, the tissue will return to the collapsed position shown. Any back pressure will force the edge of the tissue in each cusp to seal tighter against the edge of tissue in adjacent cusps.

This operation of the tissue valve is the same as in the prior art tricuspid tissue valve. What is new and improved is the method of, and structure for, assembly from prefabricated parts which permits the patient's own tissue to be used, although foreign tissue may also be used. The advantages of using the patient's tissue are quite apparent. The stents 11, 12 and flange 18 are precovered with porous cloth, such as a cloth made of Dacron, polyester fiber made from polyethylene terephthalate. In fact, the flange 18 may be made entirely out of fabric, although it is usually made of soft silastic or elastomer ring covered with cloth so that it will have some rigidity, and yet be flexible. As blood washes the fabric, tissue will grow over and onto the fabric. The result is that the prosthetic valve will be incorporated into the patient's heart. In that way the tissue may be nourished indefinitely by the patient's blood. The problem with the prior-art valves prefabricated with animal tissue is that the tissue retains some antigenicity and will elicit an antibody response so that over time the tissue will deteriorate enough to require replacement.

There is a requirement to secure the various parts of the structure together so that the valve will not become disassembled in the patient before tissue grows over it, or at any time thereafter. One approach is to precover the stents with fabric on both sides, allowing sufficient space between the stents for the seam(s) of the tissue cylinder, and allowing the fabric to extend slightly below the base of both the inner stent and the outer stent. The tissue would also be allowed to extend slightly below the base of the inner stent. Then the fabric covers of the stents and the tissue may both be quickly stitched to the flange. This technique for securing the stents and tissue to the flange 18 illustrated in FIG. 4 is comprised of manually applying stitches 21 around the entire base.

Figures 1, 2, 3, 4:
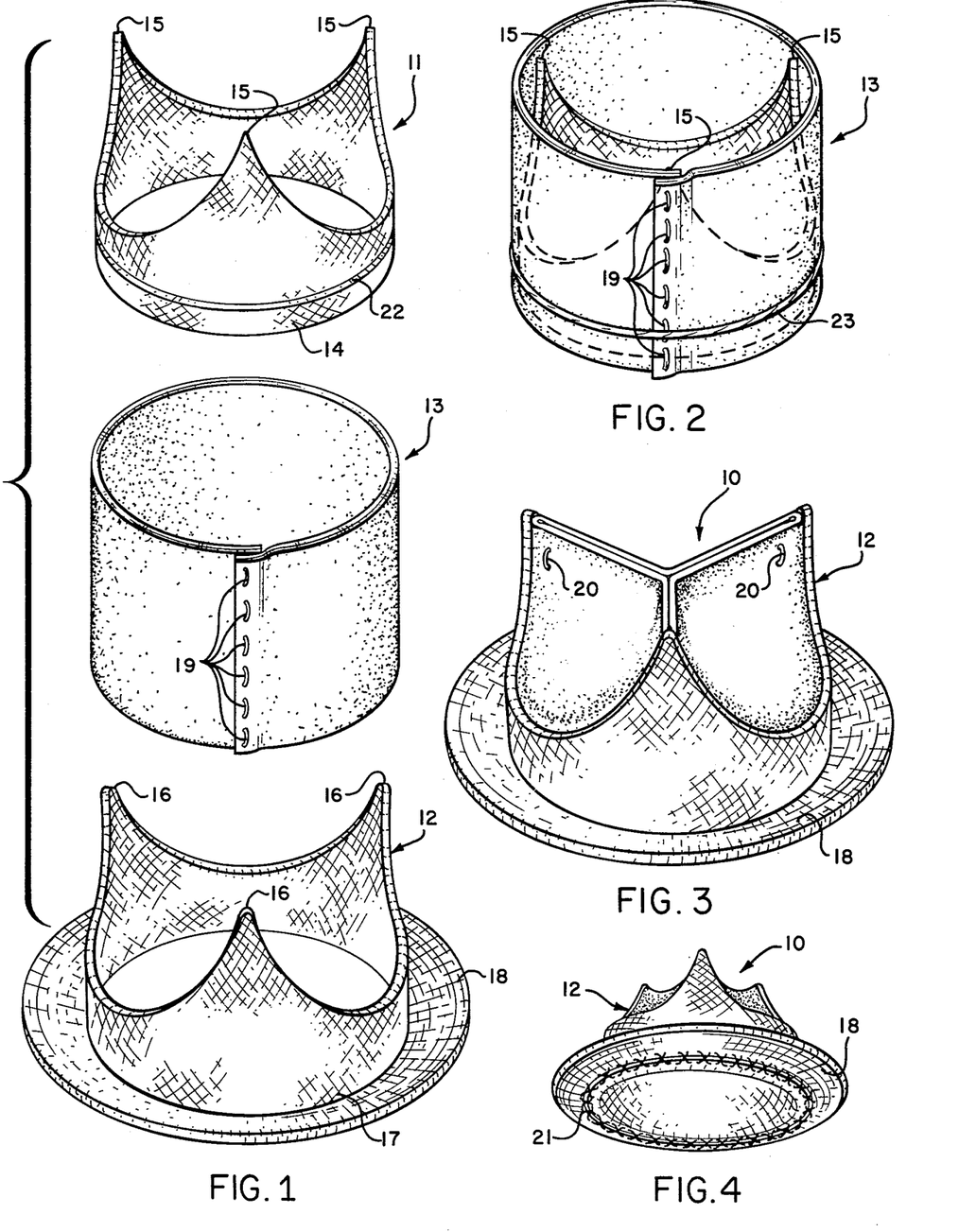
FIG. 1 is an exploded isometric view of a first embodiment of the invention.
FIG. 2 illustrates (in an isometric view) a partial assembly of the structure of FIG. 1.
FIG. 3 illustrates (in an isometric view) a complete assembly of the structure of FIG. 1.
FIG. 4 illustrates the assembly of FIG. 3 as viewed from below.

Another technique for securing the tissue cylinder in place between the stents is to provide an annular groove 22 near the base 14 of the inner stent, as shown in FIG. 1. A surgical suture 23 is then wrapped tightly around the tissue cylinder over to groove and tied. This forces the tissue over the groove to be locked in the groove. Then it is only a matter of securing the inner stent to the outer stent, as by the stitches 21 shown in FIG. 4.

Figure 5:
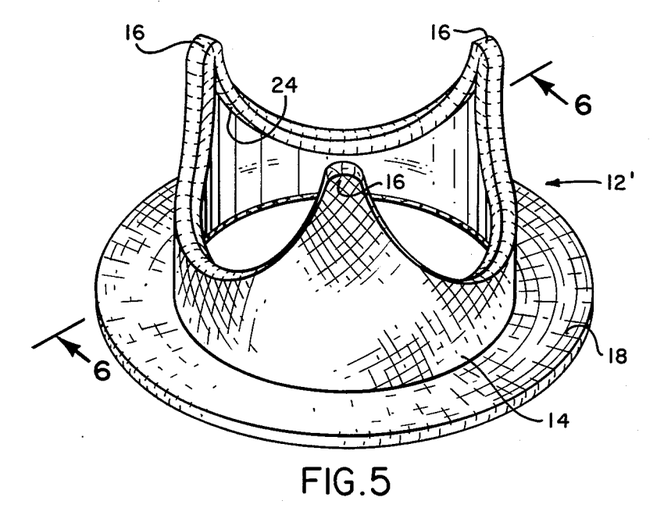
FIG. 5 illustrates a variation in the construction of the outer stent for a second embodiment.
Figure 6:
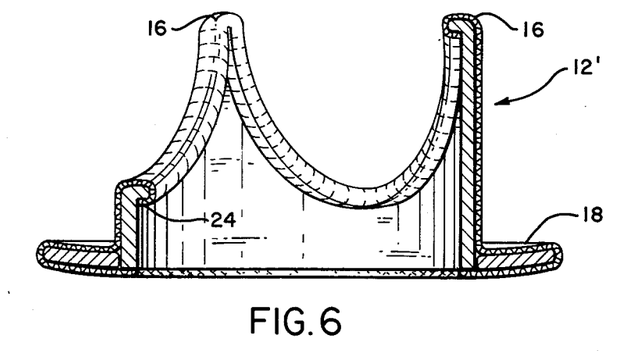
FIG. 6 is a sectional view taken on a line 6—6 in FIG. 5.
Figure 7:
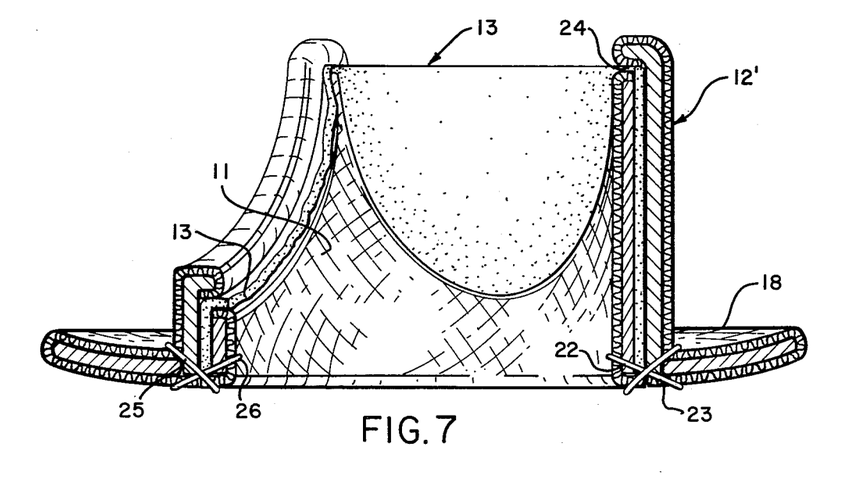
FIG. 7 is a sectional view of a complete assembly for the second embodiment corresponding to the sectional view of FIG. 6.

In a second embodiment, shown in FIGS. 5, 6 and 7, the corresponding components are identified by the same reference numerals as in the first embodiment of FIGS. 1, 2 and 3. Only the outer stent 12' is shown by itself in FIG. 5. The inner stent 11 is the same for the first embodiment, as is the tissue cylinder 13 and flange 18. What is different is only the loose fit of the stent 12', and a ledge 24 along the scalloped end of the stent 12'. This ledge traps the tissue between it and the edge of the scalloped end of the inner stent. The base of the inner stent is secured to the flange 18 by stitches 25, as shown in FIG. 7. The fabric along the bottom of the flange 18 is allowed to extend under the base of the outer stent to the base of the inner stent to facilitate this stitching. If a tight fit of the stent 12' over the tissue covered inner stent 11 is desired, the outer stent may be made with an inner diameter which does not quite allow for the thickness of the tissue. The stent 12' is then split along the center of one peak in a manner similar to that which will be described hereinafter for the embodiments shown in FIGS. 8 through 13.

From the foregoing, it is evident that a tricuspid prosthetic valve may be quickly assembled from tissue, a pair of prefabricated mating stents covered with cloth, and an annular flange, which is essentially made of Silastic rubber covered with cloth. The assembly requires only a few minutes, including any stitching used, which is very minimal. However, since the thickness of the tissue may vary from one patient to the next, it may be advantageous to split the outer stent. This is so the outer stent may be opened widely and placed over the tissue on the inner stent. Then the split end outer stent may be secured, as by stitching the cloth along the split, or even by wrapping surgical suture tightly around the base and tying the ends, just as the tissue itself may be secured on the inner stent. Still other arrangements could be provided for closing the outer stent, such as having the outer stent overlap along the split with a vascular-tooth device for locking the edges.

Figure 8:
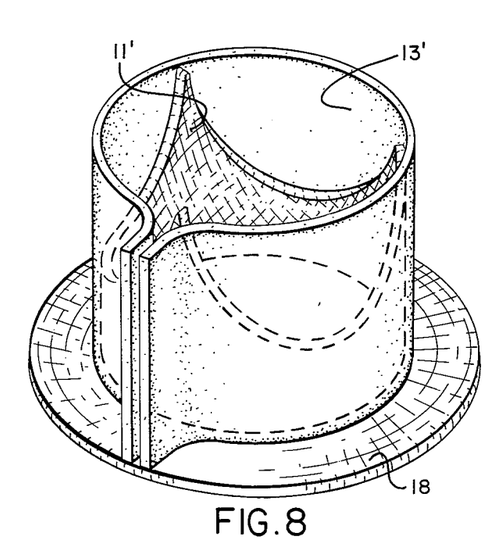
FIG. 8 illustrates (in an isometric view) a partial assembly of a third embodiment.
Figure 9:
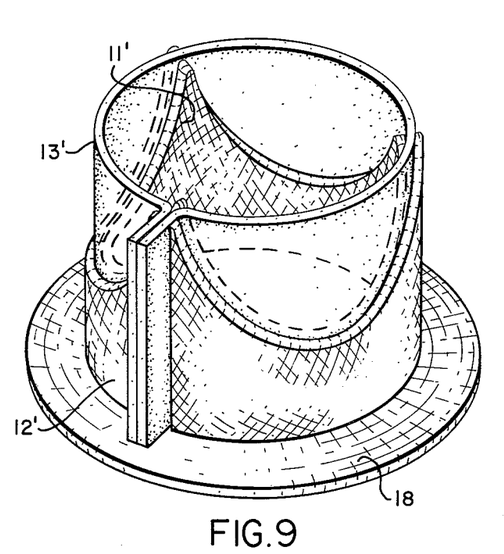
FIG. 9 illustrates (in an isometric view) the addition of an outer stent to the partial assembly of FIG. 8.
Figure 10:
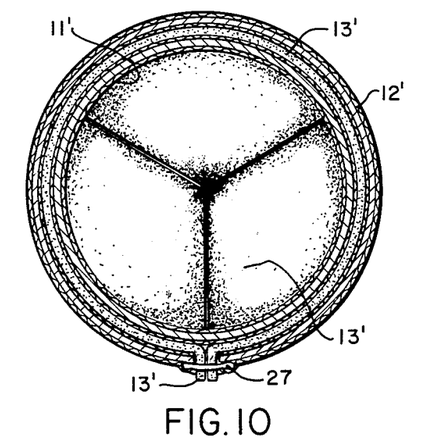
FIG. 10 is a bottom view of the assembly of FIG. 9.
Figure 11:
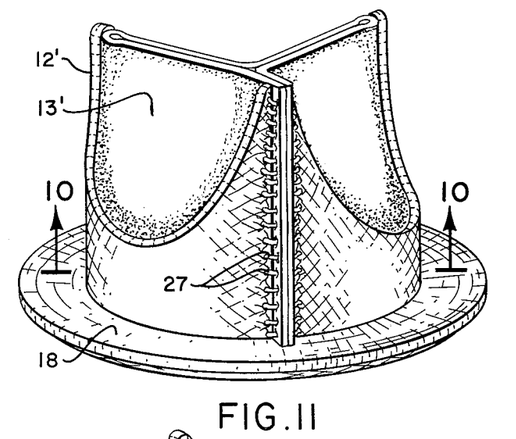
FIG. 11 is an isometric view of the complete assembly of the second embodiment illustrated in FIGS. 8, 9 and 10.
Figure 12:
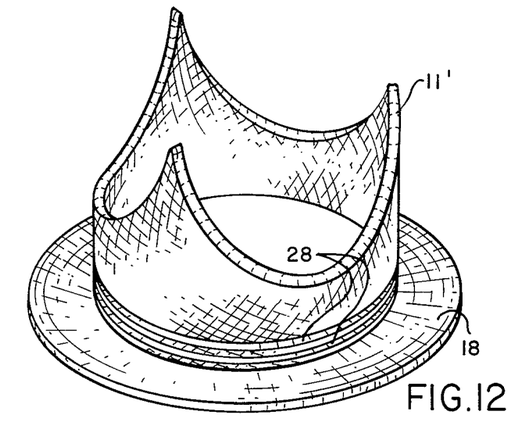
FIGS. 12 and 13 illustrate a variation in the construction of inner and outer stents for the third embodiment.
Figure 13:
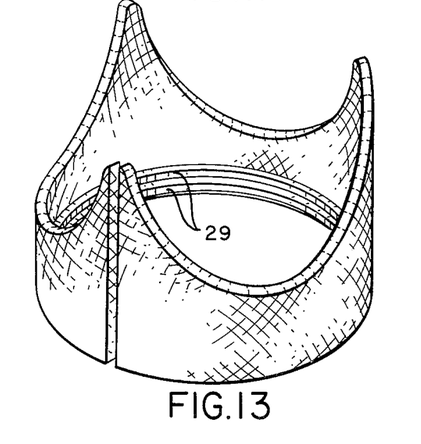

An embodiment utilizing a split outer stent is illustrated in FIG. 8. The corresponding parts are identified by the same reference numerals as in the embodiment of FIGS. 1 to 3, but with the numerals primed for those elements having some significant difference. The advantages of this embodiment is best realized when pericardium of sufficient length is available to form a tissue cylinder 13' from one piece. The tissue is wrapped around the inner stent 11', as shown in FIG. 8, and the ends are drawn together. Then a split outer stent 12' is placed over the tissue with the ends of the tissue extending through the split in the stent, as shown in FIG. 9. Next the split ends of the outer stent are stapled or sewed together by passing stitches 27 through the cloth covering the outer stent and through tissue extending through the split, as shown in FIGS. 10 and 11. The flange 18 is provided already attached to the outer stent, as shown in FIG. 11, in a manner described for the first and second embodiments. The tissue could also be tied onto the inner stent in the manner described for the first embodiment, or the inner and outer stents 11' and 12' may be provided with interlocking ridges 28 and grooves 29, or vice versa, around their bases as shown in FIGS. 12 and 13. These interlocking ridges and grooves not only clamp the tissue so it will not slip between the stents, but also interlock the stents so that one will not slip relative to the other. These grooves and ridges are to be formed in such a manner as to form an atraumatic tissue clamp, just as vascular clamps are formed for use during surgery.

A fourth embodiment will now be described with reference to FIGS. 14 and 15. The basic principal of assembling a prosthetic tricuspid heart valve from two mating stents and tissue still applies. These three elements are identified by the respective reference numerals 31, 32 and 33. The main difference is that the second stent 32 is now not an "outer" stent, but is instead made with the same internal and external diameter as the first stent 31, and is scalloped at both ends to provide a serpentine cap that fits over the scalloped end of the first stent. The tissue cylinder 33 slips over the first stent, as in the first embodiment (FIG. 2), and the second stent fits over the tissue and seats on top of the first stent, as shown in FIG. 15. Note that the second (cap) stent forces the cusps of the tissue inwardly so that the valve is effectively biased in the closed position. As a consequence, the stitches 20 used for that purpose in the first embodiment are not required, but may be included.

Aligned longitudinal holes 34 and 35 through the first (base) and second (cap) stents between the peaks 36 of the second stent provide a facility for locking the two stents together, thereby securing the tissue in place. Either a long pin or a suture may be used, by passing one end through aligned holes and carrying the other end around the outside. Either case is illustrated by a line 37 in FIG. 15 which represents either thin wire of a pin or a suture, and in each case the ends are secured at the base. The flange 38 is preattached to the base of the first stent 31.

Figure 14:
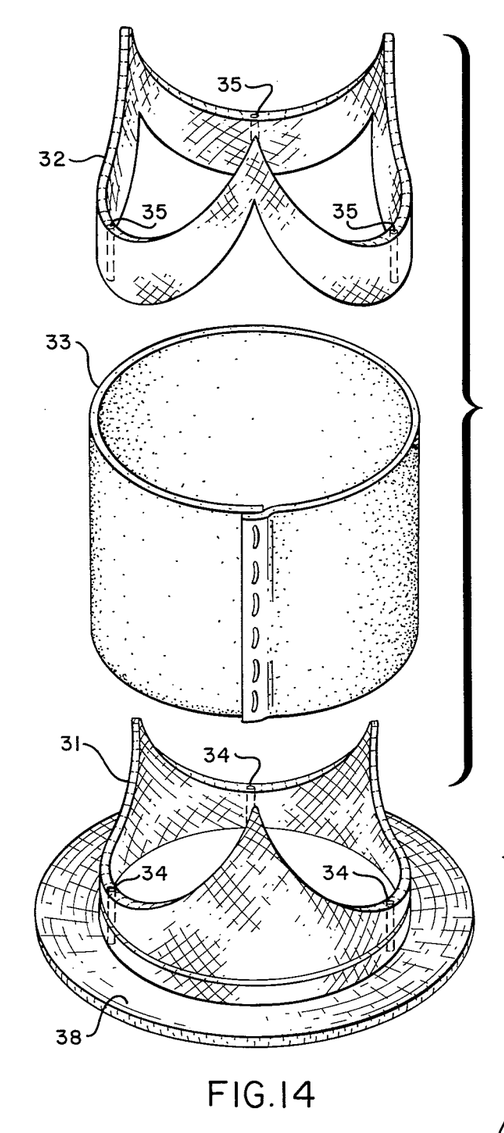
FIG. 14 is an exploded isometric view of a fourth embodiment.
Figure 15:
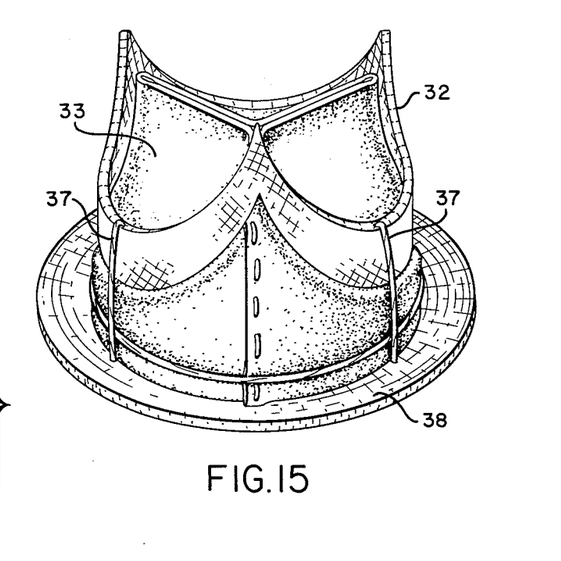
FIG. 15 illustrates (in an isometric view) a complete assembly of the structure of FIG. 14.
Figure 16:
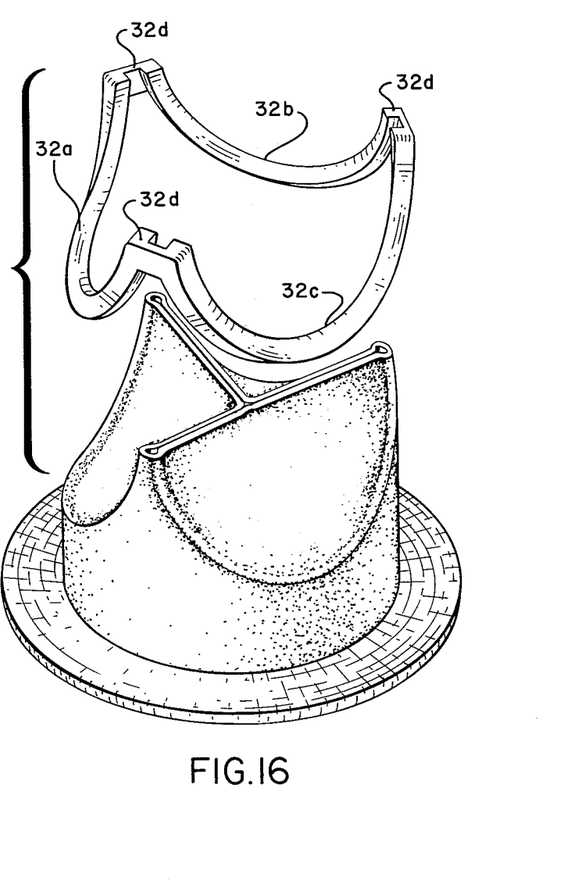
FIG. 16 illustrates in an isometric view a variant of the embodiment of FIGS. 14 and 15.

A variant of this fourth embodiment is illustrated in FIG. 16 in which the first (base) stent 31 is the same as in FIGS. 14 and 15, but the second (cap) stent is made of three rods 32a, b and c secured together at their peaks by short sections 32d welded across the peaks on the outside as shown. The rods have a round section and are covered with cloth, as are the short sections 32d, after they are welded together, although for the purpose of showing the structure, the cloth has been omitted from the drawings. The stents may be secured in the same manner as in the embodiment of FIGS. 14 and 15, or by a suture through the tissue and around the stents between the peaks.

Figure 17:
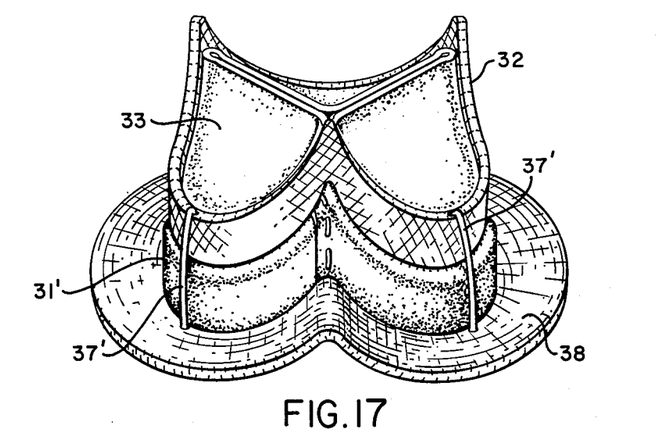
FIG. 17 illustrates in an isometric view a variant of the embodiment shown in FIGS. 14 and 15.

A second variant of this fourth embodiment is illustrated in FIG. 17, from which it is evident that the difference is only that the first (base) stent 31' is a serpentine ring very much like the second (cap) stent 32. The same technique for securing the stents, with the tissue in between, may be employed. This form of the invention is useful as a replacement of an aortic valve, while the other embodiments having a circular base are useful for replacement of an atrio-ventricular valve. In either case, the mating stents of the proper diameter are selected after the site for implantation has been prepared. Then the valve is quickly asssembled from autogenous tissue which has just been taken from the patient, or from preserved animal tissue. In the case of animal tissue, valves of various sizes may be preassembled and preserved for selection and use during surgery. The advantage in that case is only that the structure of the present invention requires less time to preassemble than prior art structures. The more significant advantage of using autogenous tissue would therefore indicate that the best mode of using the present invention is in a prosthetic tissue valve assembled at the time of surgery from tissue taken from the patient.

Figure 18:
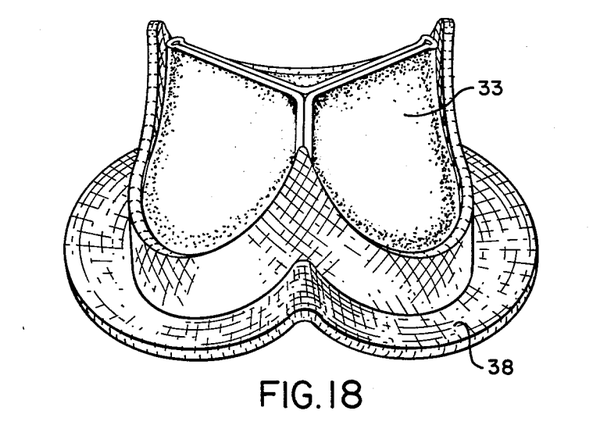
FIG. 18 illustrates in an isometric view a variant of the embodiment of FIG. 17.

FIG. 18 illustrates a variant of the embodiment shown in FIG. 17. The difference is that the second stent 32' is of larger diameter to permit it to fit around the tissue and inner stent, as in the embodiment of FIG. 3. The inner stent, which cannot be seen, is identical to the stent 31' of FIG. 17 over which the tissue is placed before the stent 32' is added. The flange 38 is preattached to the outer stent 32'. It is only necessary to secure the inner stent to the outer stent, and to secure the tissue therebetween using the techniques described hereinbefore.

A technique for fabricating a tissue valve from either autogenous tissue, such as the patient's pericardium, or foreign tissue is thus made possible by a new and improved structure comprised of two mating stents, a first (inner or base) stent and a second (outer or cap) stent, and tissue clamped therebetween. While several variations of the technique and structure have been disclosed, other variations will occur to those skilled in the art. Therefore, it is intended that the following claims cover all of the variations disclosed as well as other variations that may occur to those skilled in the art.

What is claimed is:

1. A method for fabricating a prosthetic tricuspid tissue heart valve in the limited time available during open heart surgery using two prefabricated stents that mate together with the possibility of using live tissue taken from the patient secured between the stents, at least one stent over which said tissue is placed to form a tricuspid valve from said tissue having a scalloped wall with the three peaks equally spaced apart to define three peaks of the tricuspid valve, said peaks extending approximately parallel to the axis of the one stent, comprising the steps of forming said tissue with its inside surface over the outside surface of said one stent in one or more sections, as required, to form said tricuspid heart valve using said one stent, placing the other stent in a close mating position with said one stent over the outside surface of the tissue formed on said one stent, thereby securing said tissue between stents without reliance on stitching to the stents, or other time consuming methods, and securing the inner and outer stents together with said tissue secured therebetween.

2. A method as defined in claim 1 wherein said other stent also has a scalloped wall with three peaks equally spaced apart, and said other stent is placed around said one stent over said tissue with its peaks overlaying the peaks of said one stent.

3. A method as defined in claim 1 wherein said outer stent also has a scalloped wall with three peaks equally spaced apart, and is shaped at its end opposite said peaks to conform to the scalloped end of said one stent, and wherein said other stent is fitted as a cap over said one stent with the tissue passing from outside said one stent to the inside of said other stent.

4. A method as defined in claim 2 or 3 wherein said one stent is annular and has a circular base opposite the scalloped end.

5. A method as defined in claim 2 or 3 wherein said one stent is shaped at its end opposite said peaks to conform to its scalloped end.

6. A method as defined in claim 2 wherein both stents are annular and have a circular base opposite the scalloped ends thereof.

7. The method as defined in claim 2 wherein said other stent has a ledge along its scalloped edge overhanging the scalloped end of said one stent to clamp said tissue in place.

8. A method as defined in claim 2 or 7 wherein said other stent is split to enable it to be expanded while placing it over said one stent covered with said tissue.

9. A method as defined in claim 8 wherein said tissue is a rectangular section wrapped around said one stent, and wherein free ends of said tissue extend out between the split ends of said other stent, thereby to secure the ends of the tissue.

10. A method as defined in claim 9 wherein said stents are covered with fabric, and the split in said other stent is secured by stapling or stitching through fabric and through tissue extending through the split of said other stent.

11. A method as defined in claim 8 wherein each stent is annular and has a base opposite the scalloped end thereof and both of said stents are provided with interlocking grooves and ridges around their bases to crimp the tissue and interlock said stents.

12. A method as defined in claim 1 wherein said stents are of the same size, such that said other stent fits as a cap over said one tissue covered stent, and said other stent is comprised of three rods bent to fit the scalloped walls between peaks of said one stent, and said rods are secured together at their peaks.

13. A method as defined in claim 12 wherein said bent rods are secured together by a short section of rod prewelded at each peak across the outside of the bent rods.

14. A method as defined in claim 12 or 13 wherein said bent rods have a circular section.

15. A method as defined in claim 1 wherein said stents are of the same diameter and each has a scalloped wall with three peaks equally spaced apart, said peaks extending parallel to the axis thereof, said other stent is shaped at its end opposite said peaks to conform to the scalloped end of the one stent, and said other stent is fitted over said tissue covering said one stent.

16. A method as defined by claim 1 wherein said stents are made of thermoplastic material and fabric is bonded over said stents by applying heat and pressure to said fabric and stents over at least selected areas, thereby thermobonding said fabric onto said stents.

17. A tricuspid tissue heart valve comprised of two mated stents and tissue in one or more sections, said tissue having its inner surface extending over the outer surface of one stent to form said tricuspid heart valve, said two stents mating closely together to secure said tissue between the stents, wherein at least said one stent over which said tissue is placed has a scalloped wall with three peaks equally space apart to define three peaks of the tricuspid valve, said peaks extending approximately parallel to the axis of the one stent in the direction of flow through said valve, and the other stent having a configuration to secure said tissue between it and said one stent at least along the scalloped walls of said one stent between said peaks.

18. Apparatus as defined in claim 17 wherein said other stent also has a scalloped wall with three peaks equally spaced apart, said other stent being around said one stent over said tissue with peaks of said outer stent overlaying the peaks of said one stent.

19. Apparatus as defined in claim 17 wherein said other stent also has a scalloped wall with three peaks equally spaced apart, and said other stent is shaped at its end opposite said peaks to conform to the scalloped end of said one stent, and wherein both stents are of the same size, said other stent being fitted as a cap over said one tissue with said tissue passing from outside said one stent to the inside of said other stent.

20. Apparatus as defined in claim 18 or 19 wherein said one stent is annular and has a circular base opposite the scalloped end.

21. Apparatus as defined in claim 18 or 19 wherein said one stent is shaped at its end opposite said peaks to conform to its scalloped end.

22. Apparatus as defined in claim 18 wherein both stents are annular and have a circular base opposite the scalloped ends thereof.

23. Apparatus as defined in claim 18 or 22 wherein said other stent has a ledge along its scalloped edge overhanging the scalloped end of said one stent to clamp said tissue cylinder in against the scalloped end of said one stent.

24. Apparatus as defined in claim 23 wherein said other stent is split to enable it to be expanded while placing it over the one stent covered with said tissue.

25. Apparatus as defined in claim 24 wherein free ends of said tissue extend out between the split end of said other stent, thereby to secure the ends of said tissue.

26. Apparatus as defined in claim 24 wherein each stent is annular and has a circular base opposite the scalloped end thereof and said one and said other stents are provided with interlocking annular grooves and ridges around their bases to crimp said tissue and interlock the stents.

27. Apparatus as defined in claim 17 wherein said other stent is of the same size as said one stent, such that said other stent fits as a cap over said one stent, and said other stent is comprised of three rods bent to fit the scalloped wall between peaks of said one stent, and said rods are secured together at their peaks.

28. Apparatus as defined in claim 27 wherein said bent rods are secured together at the peaks by a short section of rod at each peak welded on the outside of the stent to the ends of the rods being secured together.

29. Apparatus as defined in claim 27 or 28 wherein said bent rods have a circular cross section.

30. Apparatus as defined in claim 17 wherein said other stent also has a scalloped wall with three peaks equally spaced apart, said peaks extending parallel to the axis thereof and said other stent is shaped at its end opposite said peaks to conform to the scalloped end of the one stent, and wherein said other stent is of a larger diameter, such that the other stent fits over the one tissue covered stent.

31. Apparatus as defined in claim 17 wherein each of said stents is comprised of thermoplastic material and covered by fabric bonded thereto over at least selected areas by the application of heat and pressure to said fabric and stents thereby thermobonding said fabric onto said stents.

* * * * *